US008790328B2

(12) United States Patent
Kragelund et al.

(10) Patent No.: US 8,790,328 B2
(45) Date of Patent: Jul. 29, 2014

(54) SYSTEM FOR RECONSTITUTION OF A POWDERED DRUG

(75) Inventors: Lasse Kragelund, Frederikssund (DK); John Thrane Hansen, Vipperød (DK)

(73) Assignee: Novo Nordisk Healthcare A/G, Zurich (CH)

( * ) Notice: Subject to any disclaimer, the term of this patent is extended or adjusted under 35 U.S.C. 154(b) by 312 days.

(21) Appl. No.: 13/123,685

(22) PCT Filed: Oct. 15, 2009

(86) PCT No.: PCT/EP2009/063506
§ 371 (c)(1),
(2), (4) Date: Oct. 20, 2011

(87) PCT Pub. No.: WO2010/043685
PCT Pub. Date: Apr. 22, 2010

(65) Prior Publication Data
US 2012/0029464 A1     Feb. 2, 2012

Related U.S. Application Data

(60) Provisional application No. 61/107,412, filed on Oct. 22, 2008.

(30) Foreign Application Priority Data

Oct. 15, 2008 (EP) .................................... 08166702

(51) Int. Cl.
*A61J 1/14*     (2006.01)
(52) U.S. Cl.
USPC ............................ 604/414; 604/403; 604/411
(58) Field of Classification Search
None
See application file for complete search history.

(56) References Cited

U.S. PATENT DOCUMENTS 4,475,914 A * 10/1984 Portnoff .......................... 604/414
(Continued)

FOREIGN PATENT DOCUMENTS

CN          1874812 A        12/2006
(Continued)

OTHER PUBLICATIONS

Non-Final Office Action Mailed Jun. 22, 2009 in U.S. Appl. No. 12/298,082 Filed Oct. 22, 2008; First Named Inventor: Radmer.

(Continued)

*Primary Examiner* — Tan-Uyen T Ho
*Assistant Examiner* — Eric Bryant
(74) *Attorney, Agent, or Firm* — Wesley A. Nicolas; Reza Green; Richard W. Bork

(57) ABSTRACT

A mixing system (1) adapted to allow first contents of a first container (2) and second contents of a second container (3) to mix to form a material. The mixed material is retrieved to a syringe (20) without being foamed. The mixing system (1) comprises a transfer unit (5) which is adapted to receive the first container (2) at a first port (11), the second container (3) at a second port (12) and the syringe (20) at a third port (13). The transfer unit (5) further houses a number of fluid pathways (14, 15, 16) interconnecting the three ports (11, 12, 13) as well as a number of flow control members (17, 18, 19, 22) for controlling fluid flow between the containers (2, 3) and the syringe (20). At least one of the flow control members (17, 18, 19, 22) allows a user to switch between two states of fluid flow, one in which fluid flow is enabled between the first port (11) and the third port (13) as well as between the third port (13) and the second port (12), and one in which fluid flow is enabled between the second port (12) and the third port (13). The invention also relates to a transfer unit comprising first and second ports for receiving first and second containers, respectively, a third port for coupling to a syringe, a number of fluid pathways interconnecting the ports, at least one flow control member which allows a user to switch between two states of fluid flow, and a locking means to ensure that the at least one flow control member can only be manipulated when a syringe is coupled to the third port.

13 Claims, 12 Drawing Sheets

(56) References Cited

U.S. PATENT DOCUMENTS

| | | | |
|---|---|---|---|
| 4,509,861 A * | 4/1985 | Sjonell | 366/131 |
| 4,543,101 A | 9/1985 | Crouch | |
| 4,900,322 A * | 2/1990 | Adams | 604/410 |
| 5,466,220 A | 11/1995 | Brenneman | |
| 5,466,228 A * | 11/1995 | Evans | 604/248 |
| 6,099,511 A * | 8/2000 | Devos et al. | 604/246 |
| 6,355,024 B1 * | 3/2002 | Small et al. | 604/500 |
| 6,364,865 B1 | 4/2002 | Lavi et al. | |
| 6,475,183 B1 | 11/2002 | Epstein et al. | |
| 2006/0027270 A1 * | 2/2006 | Truitt et al. | 137/843 |
| 2007/0024458 A1 | 2/2007 | McGinty et al. | |
| 2007/0088252 A1 * | 4/2007 | Pestotnik et al. | 604/82 |
| 2007/0106244 A1 | 5/2007 | Mosler et al. | |
| 2007/0131296 A1 * | 6/2007 | Schinazi et al. | 138/43 |
| 2007/0219597 A1 * | 9/2007 | Kamen et al. | 607/60 |
| 2008/0009790 A1 | 1/2008 | Delay | |
| 2008/0195031 A1 * | 8/2008 | Kitani et al. | 604/19 |
| 2010/0191106 A1 * | 7/2010 | Koyama | 600/431 |

FOREIGN PATENT DOCUMENTS

| | | | | |
|---|---|---|---|---|
| CN | 101073535 A | 11/2007 | | |
| FR | 2850015 | 7/2004 | | |
| WO | WO 9311709 | 6/1993 | | |
| WO | WO 9406690 | 3/1994 | | |
| WO | WO 9531955 | 11/1995 | | |
| WO | WO 9926581 | 6/1999 | | |
| WO | WO 0147571 | 7/2001 | | |
| WO | WO 2005120431 | 12/2005 | | |
| WO | WO 2006/124634 | * 11/2006 | | A61M 5/19 |
| WO | WO 2007101786 | 9/2007 | | |
| WO | WO 2007/122209 | * 11/2007 | | A61M 5/178 |
| WO | WO 2007122209 | 11/2007 | | |
| WO | WO 2007/147741 | 12/2007 | | |
| WO | WO 2008048323 | 4/2008 | | |

OTHER PUBLICATIONS

Final Office Action Mailed Jan. 25, 2010 in U.S. Appl. No. 12/298,082 Filed Oct. 22, 2008; First Named Inventor: Radmer.

Examiner'S Answer to Appeal Brief Mailed Oct. 22, 2010 in U.S. Appl. No. 12/298,082 Filed Oct. 22, 2008; First Named Inventor: Radmer.

English Abstract of FR2850015 Published Jul. 23, 2004.

* cited by examiner

SYSTEM FOR RECONSTITUTION OF A POWDERED DRUG

CROSS-REFERENCE TO RELATED APPLICATIONS

This application is a 35 U.S.C. §371 national stage application of International Patent Application PCT/EP2009/063506 (published as WO 2010/043685), filed Oct. 15, 2009, which claimed priority of European Patent Application EP 08166702.4, filed Oct. 15, 2008; this application further claims priority under 35 U.S.C. §119 of U.S. Provisional Application 61/107,412, filed Oct. 22, 2008.

The present invention relates to the mixing of substances, e.g. of an active powdered drug and a solvent or diluent, for the preparation of a product that can be administered to the body by e.g. injection or infusion.

BACKGROUND OF THE INVENTION

It is well known in the art that the storage life of certain injectable substances, such as glucagon, is increased when the substance is stored in a powdered state. Lyophilization is one way of producing a powdered substance from a liquid based material. It involves a rapid freezing of the material at a very low temperature followed by a rapid dehydration by sublimation in a high vacuum. The resulting lyophilized substance is typically stored in a glass vial or cartridge which is closed by a cap, such as a rubber stopper or septum.

It is necessary to reconstitute the powdered or solid substance prior to administration. This is accomplished by mixing the powdered substance with a suitable diluent or liquid. Reconstitution is traditionally performed using a syringe with a needle to withdraw the diluent from one separate vial and inject it into another separate vial containing the powdered compound, whereupon the latter vial is shaken or swirled to thoroughly mix the two constituents. The syringe with needle is then used to withdraw from this vial the desired amount of reconstituted drug to be injected into the patient. Because two separate containers are used, the person reconstituting the compound must be certain to mix the correct amounts such that a proper concentration of the mixture results. When a syringe is used to mix the diluent and the drug, an exact diluent to drug ratio is difficult to obtain. This brings about some uncertainty regarding the exact concentration of administered drug.

Moreover, because the diluent and the compound are in separate, sterilized containers, and the diluent is manually withdrawn from the diluent container via a syringe with a needle, and the syringe is subsequently moved from the diluent container to the compound container for injection of the diluent into the compound container, both sterility and safety are in risk of being compromised.

Because of an increased use of powdered compounds or lyophilized drugs it is desirable to provide both professionals and non-professionals with a simple and reliable system that facilitates preparation of an accurate dosage of a mixed product, e.g. a reconstituted compound.

In addition, it is desirable to provide a system that can reconstitute a lyophilized drug without potential hazards to the user while maintaining sterility throughout the process.

U.S. Pat. No. 5,466,220 discloses a mixing device comprising a base on which a syringe and two vials are mounted together with a T-shaped connector piece. Retainers hold the two vials in place at a predetermined spacing from their respective connectors prior to operation of the device. The device is kept within a protective sterile packaging until the vials are pushed into their respective connectors allegedly providing a system that is sealed during the entire reconstitution process.

U.S. Pat. No. 6,364,865 discloses different embodiments of medication delivery systems and transfer systems for forming a solution from constituents from a set of vials respectively containing a lyophilized compound and a diluent.

Sometimes a desired dose of a drug solution exceeds the amount corresponding to the drug contained in a single set of vials. In this case the total dose must be composed using lyophilized drug from two or more vial sets, the number of vial sets corresponding to the desired dose. This may, e.g., be done by sequentially applying a solvent liquid to each of the vials and retrieving the reconstituted drug to one common reservoir or syringe. When the drug of all of the vials has been reconstituted in this manner, the total dose may be administered to the person from the common reservoir or syringe. Reconstituting lyophilized drug from two or more vials in this manner is, however, relatively time consuming. Furthermore, there is a risk of contamination of the drug due to the number of times a free opening will be exposed to free air or dirt.

It is therefore desirable to provide a mixing system which facilitates mixing a dose using powdered drug from two or more vials, also known as pooling, and which reduces the risk of contamination of the resulting drug.

WO 2007/122209 discloses a transfer system comprising a container unit holding two containers and a transfer unit adapted to be coupled to the container unit for enabling a mixing of the contents of the two containers, wherein a pressure generator, such as a syringe, is used to force the contents of the one container to move to the other container via a channel in the transfer unit fluidly connecting the two containers.

When emptying the container containing the final mixed product the influence of included air should be minimised in order to avoid foaming of the drug. Two factors which may contribute to the generation of foam in a system as described in WO 2007/122209 are the flow rate of the drug solution when transferred from the container to the syringe and air that is potentially aspired from other parts of the system such as the solvent container.

It is desirable to provide a mixing system which substantially eliminates the issue of foaming. Avoiding foaming is highly important for several kinds of drugs, in particular drugs that must be given intravenously, such as recombinant factor products for the treatment of haemophilia patients.

SUMMARY OF THE INVENTION

Having regard to the above mentioned problems and deficiencies, it is an object of the present invention to provide a mixing device, which is simple and efficient for users to operate and which provides for a sterile preparation of an accurate dosage of administrable drug.

A further object of the invention is to provide a mixing system for reconstituting a powdered drug, which substantially eliminates foaming of the final reconstituted product.

An even further object of the invention is to provide a mixing system that is simple and cost efficient to produce.

In the disclosure of the present invention, aspects and embodiments will be described which will address one or more of the above objects or which will address objects apparent from the below disclosure as well as from the description of exemplary embodiments.

In a first aspect of the invention a medical mixing system is provided comprising a first container containing first contents, a second container containing second contents, and a transfer unit. The transfer unit comprises a first port adapted to receive the first container, a second port adapted to receive the second container, a third port adapted to receive a syringe, a first fluid pathway that enables fluid flow between the first port and the third port, a second fluid pathway that enables fluid flow between the third port and the second port, a third fluid pathway that enables fluid flow between the second port and the third port, a first flow control member disposed between the first port and the third port, enabling one-way fluid flow from the first port to the third port when a syringe is coupled to the third port, a second flow control member disposed between the third port and the second port, enabling one-way fluid flow from the third port to the second port when a syringe is coupled to the third port, and a third flow control member. The third flow control member provides for user selective switching between a first state in which fluid flow is enabled between the first port and the third port via the first fluid pathway and between the third port and the second port via the second fluid pathway, and a second state in which fluid flow is enabled between the second port and the third port via the third fluid pathway but disabled between the first port and the third port.

By the above mixing system, the syringe is allowed to receive the first contents from the first container and to transfer the first contents to the second container, respectively receive a volume of material which has been formed by mixing the first contents and the second contents.

The above arrangement enables a user to perform the transfer of the first contents from the first container to the second container and the transfer of the mixed product from the second container to the syringe in a safe way while maintaining sterility during the whole procedure. Further, the steps of withdrawing the plunger in the syringe, which causes the first contents to move from the first container to the syringe, and subsequently advancing the plunger in the syringe, which causes the first contents to move from the syringe to the second container, are intuitively comprehensible and easy to carry out by the user as they resemble the traditional steps for transferring a medium from one container to another using a syringe with a needle.

The first contents may be a liquid material, such as a diluent which is suitable as a solvent for a powdered or lyophilized drug, and the second contents may be a dry material, such as a powdered or lyophilized drug. In this case the material formed when the first contents and the second contents are mixed is a reconstituted drug being ready for delivery to a user, e.g. by means of infusion or injection. Alternatively, the first contents as well as the second contents may be liquid materials.

The first container may be any suitable kind of container, such as a vial, a flexible container, etc. Similarly, the second container may be any suitable kind of container.

Generally, when a powdered drug has been reconstituted, great care must be taken to assure that the drug solution does not foam during the transfer to the syringe as this may introduce a risk of the user subsequently injecting or infusing volumes of air into the bloodstream or tissue along with the drug solution.

Thus, in an embodiment of the invention, the transfer unit of the mixing system further comprises a fourth flow control member in the third fluid pathway for substantially eliminating foaming when the drug solution formed by the mixing of the first and second contents is transferred to the syringe. In a specific preferred embodiment, the fourth flow control member acts to reduce/restrict the flow rate of the drug solution when the third flow control member is positioned so that fluid flow from the second port to the third port via the third fluid pathway is enabled. The fourth flow control member would constitute a cross-sectional area reduction of the third fluid pathway.

According to one embodiment, fluid flow from the first port to the third port is enabled when the fluid pressure in the third port exceeds a predefined negative pressure, caused by withdrawing a plunger of the syringe. According to this embodiment, the first contents may be moved from the first container to the syringe via the first fluid pathway due to a decrease in pressure at the third port. The aspiration of the first contents from the first container may cause a negative pressure build-up in the first container. This negative pressure can be compensated by allowing ambient air to enter into the first container. One way to allow ambient air to enter into the first container is to provide a vent in the transfer unit that enables air flow between the outside and the first port.

Alternatively, a pre-established positive pressure in the first container could provide the fluid flow from the first port to the third port automatically when the syringe is connected to the third port.

In one embodiment, the first port comprises two channels. One of these channels may be a liquid channel dedicated to the transfer of the first contents out of the first container while the other channel may be an air channel being fluidly connected to a vent to allow for air flow between the first container and the outside. The vent may be provided with a fifth flow control member enabling one-way fluid flow from the outside to the first container.

In such a construction air bubbles may enter the liquid channel when the first contents is moved from the first container to the syringe. However, if the air channel opening is arranged above the liquid channel opening during aspiration of the first contents from the first container, essentially no air will be transferred along with the first contents.

In one embodiment, the first container is provided with a closure, e.g. in the form of a penetrable membrane, in order to ensure sterility of the first contents. The first port is adapted to penetrate this membrane to establish fluid connection between the first container and the first fluid pathway. In case the penetration is performed by two individual piercing members, e.g. two needles, the connecting interface may be unstable, e.g. due to the relatively small dimensions, which may result in breakage of one or both of the individual piercing members. Furthermore, the introduction of two individual piercing members through the membrane increases the risk of leakage of the first contents from the first container.

Thus, in an embodiment of the invention the first port comprises an asymmetric hollow spike or needle having two internal channels, the openings of which are axially offset to allow for transfer of the first contents from the first container to the third port with essentially no inclusion of air.

The transfer unit may comprise a filter arranged in the vent to further minimise the risk of contamination of the first contents in case any air bubbles should, unexpectedly, enter the liquid channel.

Alternatively or additionally, the transfer system may comprise a filter arranged in the third fluid pathway. Such a filter can be used for preventing impurities from being transferred from the second container to the syringe when the drug solution is transferred to the syringe. Such impurities could, e.g., be rubber particles originating from a stopper of a vial and being created during penetration of the stopper, and/or dry contents which has not been properly solved.

The syringe may in the above described arrangements be connected to the transfer unit in a state where the plunger is fully advanced. This will provide for a perfectly sterile mixing system as no contaminated air is allowed to enter the system during a mixing procedure.

When the spike penetrates the closure of the first container a positive pressure may be generated in the first container, potentially leading to a small volume of the first contents being forced out through the spike. If the vent is not provided with a flow control member preventing fluid flow from the first container to the outside this volume of the first contents may be forced completely out of the transfer unit whereby it will be lost to the surroundings. This is definitely undesirable as it will lead to an imbalance in the volumetric relationship between the first contents and the second contents, resulting in the final mixed product getting a higher potency than intended. Furthermore, the user will experience a leaking device, which may cause him to question the reliability of the product.

In another aspect of the invention a medical mixing system is provided comprising a first container containing first contents, a second container containing second contents, and a transfer unit. The transfer unit comprises a housing, a first port adapted to receive the first container, a second port adapted to receive the second container, a third port adapted to receive a variable volume reservoir, e.g. a syringe, a plurality of fluid pathways for interconnecting the first port, the second port, and the third port, e.g. as described above in relation to the first aspect, and a reservoir in fluid communication with the first port.

In a particular embodiment the first port comprises a dual channel spike, and the reservoir is in fluid communication with one of the channels in the spike.

The reservoir may further be in fluid communication with ambient air, e.g. via an opening in the transfer unit housing, and it may comprise a serpentine channel segment of which the end portion is in direct fluid communication with the ambient air. Thereby a tortuous path is provided reducing the risk of the escaped volume of the first contents leaking out of the reservoir during user preparation of the mixing system.

By including a reservoir in the transfer unit leakage of the first contents is effectively prevented because any escaped material will accumulate in the reservoir, and once the user commences the mixing procedure by sucking the first contents out of the first container the small volume of first contents which may have escaped through the spike at penetration of the container closure will simply be drawn from the reservoir back into the first container and further into the first fluid pathway along with the bulk of the first contents. Thereby it is ensured that the entire volume of the first contents is aspired into the syringe and used for mixing with the second contents, i.e. that the final administrable drug has the prescribed potency.

When the first contents have been transferred to the second container to mix with the second contents the user may operate the third flow control member to allow transfer of the mixed product from the second container to the syringe. This may be done by forcing the third flow control member to move from a first position to a second position in the transfer unit, e.g. by rotating the third flow control member in the transfer unit housing. The third flow control member may be in the form of a plug comprising an axi-symmetric, e.g. a circular cylindrical or conical, plug body adapted to fit tightly in the transfer unit housing and an enlarged grip portion enabling the user to rotate the third flow control member from outside the transfer unit housing.

The plug body may be provided with channel segments arranged in such a manner that when the third flow control member is in the first position a first channel segment constitutes a portion of the first fluid pathway and a second channel segment constitutes a portion of the second fluid pathway, and when the third flow control member is in the second position a third channel segment constitutes a portion of the third fluid pathway. Importantly, when the third flow control member is in the second position there is no fluid connection between the first port and the third port, whereby it is ensured that no air is introduced via the first fluid pathway in the transfer of the mixed product from the second container to the syringe. The mixed product is therefore not in risk of being contaminated by ambient air, just as the risk of foaming is minimised.

In a particular embodiment the first channel segment and the second channel segment share a channel segment portion.

The channel segments may be arranged on the surface of the plug body, e.g. as grooves in the plug material, and may be circumferentially separated in such a manner that when the third flow control member is in the first position the first channel segment completes the first fluid pathway and the second channel segment completes the second fluid pathway while the third fluid pathway is disconnected, and when the third flow control member is in the second position the third channel segment completes the third fluid pathway while the first fluid pathway and the second fluid pathway are disconnected, respectively.

The particular arrangement of the channel segments on the surface of the plug body determines the angular movement of the third flow control member required to switch between the first state and the second state. In a specific embodiment the channel segments are arranged such that a substantially 90 degrees rotation of the third flow control member is required to switch between the first state and the second state.

If the channel segments are arranged on the surface of the plug body it is important to provide a fluid tight fit between the plug and the transfer unit housing. Otherwise, a part of the liquid being transferred may in fact leak out of the housing along the plug body. On the other hand, since the third flow control member is user operable the fit should not be so tight as to cause a high friction interface that makes the third flow control member difficult to rotate.

In a further aspect of the invention a flow control member for a fluid transfer unit, e.g. as described in the above, is provided comprising an axi-symmetric body of a first material, a grip portion for user operation, and two or more channel segments arranged on the surface of the axi-symmetric body, wherein the channel segments are defined by at least one ridge.

The at least one ridge may be of a second material different from the first material in which case the flow control member may be manufactured using a two-component moulding process. The first material may e.g. be a thermoplastic polymer, such as HDPE, and the second material may e.g. be a thermoplastic elastomer, such as TPV, or a thermoset elastomer.

By providing such a dual component body the sealing capability of the flow control member is improved considerably, while a low friction is established between the contacting surfaces of the transfer unit and the flow control member. This allows the user to rotate the flow control member applying only a slight torque.

The third port may comprise a connector for coupling with the syringe. The syringe may e.g. be of the Luer lock type comprising an internally threaded retaining collar, and the connector may e.g. comprise an external screw thread onto which the syringe can be attached. Alternatively, other types of connections between the syringe and the third port may be employed, such as e.g. a press-fit or a bayonet coupling. In relation to the attachment of the syringe to the third port it is important that the syringe cannot be forced, e.g. screwed, too far onto the connector since this may cause the tapered outlet portion of the syringe to break rendering both the syringe and the transfer unit useless.

In a further aspect of the invention a transfer unit for a medical mixing system is provided comprising a housing, a first port adapted to receive a first container, a second port adapted to receive a second container, a third port adapted to receive a variable volume reservoir, e.g. a syringe, a plurality of fluid pathways for interconnecting the first port, the second port, and the third port, e.g. as described above, and a contact face adapted to abut with the variable volume reservoir when the variable volume reservoir is coupled with the third port.

The contact face may be arranged at the third port and may be adapted to abut with a contact face of the syringe, e.g. a retaining collar of a Luer lock syringe, so as to provide a distinct stop for further translatory movement of the syringe relative to the transfer unit in the direction of attachment.

Such a distinct stop will provide a safety against the syringe being mishandled during attachment to the transfer unit, e.g. against the syringe being screwed too far onto a connector of the third port, because the user will be able to differentiate between proper and improper attachment. The user will simply sense the abutment between the contact face of the transfer unit and that of the syringe and will intuitively know that no further movement is needed.

According to one embodiment, fluid flow from the third port to the second port is enabled when the syringe plunger is advanced to expel the first contents out of the syringe and into the second fluid pathway. This will move the first contents to the second container and create an excess pressure in the second container due to the compression of the air molecules present therein. The system will remain in this pressurised condition until the third flow control member is manipulated to enable fluid flow from the second port to the third port via the third fluid pathway. Such a manipulation will result in the drug solution being forced out of the second container and into the third fluid pathway by the expanding air.

If a syringe is not coupled to the third port at the time where the third flow control member is manipulated to enable fluid flow from the second port to the third port via the third fluid pathway, some or all of the drug solution may just flow out of the system through the third port and be wasted to the surroundings.

Thus, in a further aspect of the invention a transfer unit for a medical mixing system is provided comprising a first port adapted to receive a first container containing first contents, a second port adapted to receive a second container containing second contents, a third port adapted to receive a variable volume reservoir, a plurality of fluid pathways for interconnecting the first port, the second port, and the third port, e.g. as described above in relation to the first aspect, and a user operable flow control member enabling user selective fluid flow from the second port to the third port, wherein the transfer unit further comprises a locking means adapted to engage with the user operable flow control member to prevent movement of the user operable flow control member, and wherein the locking means is configured to disengage with the user operable flow control member in response to a variable volume reservoir being coupled to the third port. The transfer unit may further comprise any features and elements mentioned in connection with the above aspects.

The locking means is provided to ensure that the user operable flow control member can only be manipulated to enable fluid flow from the second port to the third port when a variable volume reservoir, such as a syringe, is coupled to the third port.

According to one embodiment the locking means comprises a mechanical engagement between a catch member and the user operable flow control member, e.g. between a protrusion and a recess. The catch member may be biased so that the user operable flow control member is maintained in its position by the mechanical interaction between the catch member and the user operable flow control member as long as a syringe is not coupled to the third port. When a syringe is coupled to the third port a mechanical interface between the syringe and the locking means will provide for a release mechanism that moves the catch member out of engagement with the user operable flow control member, thus allowing for manipulation of the user operable flow control member.

The bias on the catch member may be provided by a structure of which the catch member itself is a part. Alternatively, or additionally, the bias may be provided by one or more separate resilient elements.

The locking means may further be configured to re-engage with the user operable flow control member in response to the variable volume reservoir being decoupled from the third port.

The mechanical engagement between the catch member and the user operable flow control member may be realised by an interaction between a protrusion and a recess. The recess may be provided in the user operable flow control member or, alternatively, in the locking means. Hence, the catch member may comprise a protrusion or a recess.

In a particular embodiment the locking means has an elastically deformable geometry and is arranged in the transfer unit in such a manner that it biases the catch member towards the user operable flow control member. This ensures that the catch member re-engages with the user operable flow control member to lock the user operable flow control member in position when the syringe is removed from the third port.

The catch member may be an integral part of the locking means or it may be a separate element suitable for physical connection with the locking means.

The provision of a locking means as described above in connection with a fluid tight system, also as described above, enables the user to prepare one or more containers containing a drug solution or mixed material for subsequent transfer to a syringe without having to worry about the concentration or the sterility of the drug solution. Pooling of the contents of several containers is thereby safe and easy.

In a further aspect, the invention relates to a container unit for a medical mixing system according to the first aspects, the container unit comprising a first container containing first contents and a second container containing second contents to be mixed with said first contents.

In an embodiment of the invention the containers are pre-arranged in the container unit by the manufacturer, and it can thereby be ensured that the first contents and the second contents match, e.g. in terms of amount and kind. Accordingly, when the first contents and the second contents are mixed, the risk of errors occurring during mixing of the contents is thereby minimised. The containers are preferably irremovably arranged in a mutually fixed position in the container unit.

The first and second container may alternatively be provided as separate containers, i.e. not fixed in the same housing.

The container unit and the transfer unit are adapted to be coupled together to form a mixing system or a mixing kit. The units may advantageously be delivered together in one package. In order to mix the first contents and the second contents, the user must couple the units together, and possibly operate one or more features of the transfer unit, e.g. one or more flow control members and/or a plunger of a syringe, in order to cause the first contents to move to the second container or the drug solution to move to the syringe. Thereby the container unit may be maintained under sealed conditions during storage. This increases the expected lifetime of the contents of the containers, and counteracts contamination of the contents. Finally it is a large advantage for the manufacturer to produce the container unit separately as the number of parts requiring absolute sterile production facilities is minimised, i.e. minimal production complexity. Thus, the invention provides a mixing system that is simple and cost efficient to produce.

Furthermore, by providing the container unit and the transfer unit as a kit it can be ensured that the transfer unit is actually suitable for mixing the contents of the first and second containers.

The container unit and the transfer unit may be shaped in such a manner that they can only be coupled together when being positioned at a predetermined mutual orientation. According to this embodiment, it can be ensured that the first container is coupled to the first port and the second container is coupled to the second port when the container unit and the transfer unit are coupled together. Thereby it is also ensured that the first container, the second container and the syringe are interconnected in a correct manner by the flow channels, and that the fluid flows in the transfer unit during mixing of the first and second contents are as expected. Accordingly, a correct mixing of the first contents and the second contents can be ensured. A way of ensuring a predetermined mutual orientation is to shape the container unit and the transfer unit in an asymmetric manner, e.g. so that each has a straight edge and a curved edge opposing the straight edge.

In a further aspect of the invention a method for mixing substances is provided, comprising a) coupling a container unit, comprising a first container and a second container, and a fluid transfer unit comprising first coupling means for establishing fluid connection to the first container, second coupling means for establishing fluid connection to the second container, third coupling means for establishing fluid connection to a variable volume reservoir, a plurality of fluid pathways interconnecting the first coupling means, the second coupling means and the third coupling means, and a flow control member, b) attaching a variable volume reservoir to the third coupling means, c) increasing the volume of the variable volume reservoir, and d) decreasing the volume of the variable volume reservoir.

The fluid transfer unit may further comprise a user operable flow control member, and the method may further comprise e) turning the user operable flow control member from a first position to a second position, and f) increasing the volume of the variable volume reservoir.

The latter steps of the method will ready the mixed product for direct administration from the variable volume reservoir, e.g. via an infusion set, once the variable volume reservoir has been detached from the third coupling means.

The variable volume reservoir may comprise a syringe, e.g. a Luer lock syringe, or indeed any kind of container capable of increasing and decreasing its internal volume, such as a flexible bag.

In the present specification reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in at least that one aspect or embodiment of the invention, but not necessarily in all aspects or embodiments of the invention. It is emphasized, however, that any combination of features, structures and/or characteristics described in relation to the various aspects and embodiments of the invention is encompassed by the invention unless otherwise indicated herein or clearly contradicted by context.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "inwards" and "outwards", are used, these refer to the appended figures and not necessarily to an actual situation of use. The shown figures are schematic representations for which reason the configuration of the different structures as well as their relative dimensions are intended to serve illustrative purposes only.

The following text provides a description of exemplary embodiments of the invention.

The present invention is directed to systems for reconstituting a dry drug by mixing the dry drug with a solvent or liquid. The reconstitution system includes a transfer unit which is able to connect to a couple of containers, respectively a variable volume reservoir, such as a syringe, and which enables subsequent transfer of the contents of the one container to the other. The transfer unit further enables transfer of the final drug solution to the syringe.

Figure 1:
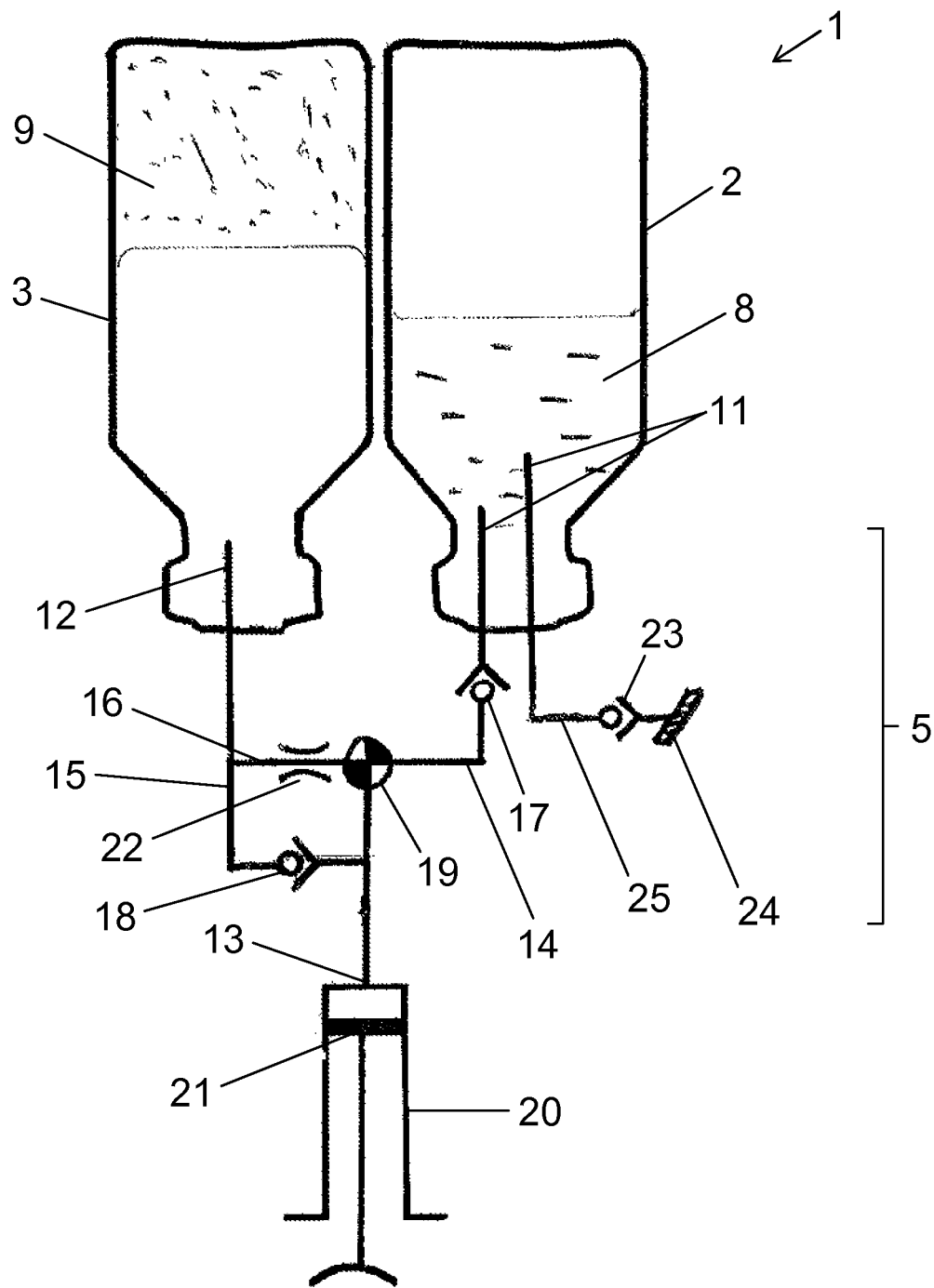
FIG. 1 shows a schematic view of a mixing system according to an embodiment of the invention.

FIG. 1 shows a schematic representation of a mixing system 1 in which a first container 2, containing a predetermined amount of a diluent 8, a second container 3, containing a predetermined amount of powdered drug 9, and a syringe 20 are connected to a transfer unit 5.

In the depicted embodiment, the two containers 2 and 3 are formed as standard vials each having a piercable septum closing the vial and having a retaining cap for fixedly retaining the septum.

Transfer unit 5 comprises a housing 10 (see FIGS. 4 and 7) which houses the necessary fluid pathways, control members and ports. The housing 10 may be designed to receive the two containers 2 and 3, so that they are partly or fully accommodated inside the housing 10. Alternatively, the housing 10 may be designed to only encircle the cap parts of the vials.

Transfer unit 5 is provided with a first port 11 adapted to receive the first container 2 and a second port 12 adapted to receive the second container 3. The ports 11 and 12 may be adapted to receive each of the two containers 2 and 3 in a first condition and a second condition. In the first condition, the two containers 2 and 3 are only retained in the housing and no fluid communication to the interior of the two containers 2 and 3 is established. In this first condition, the transfer system 5, including the two containers 2 and 3, can be stored long term. In the second condition fluid communication is established between the fluid pathways of transfer unit 5 and containers 2 and 3.

The coupling ports 11 and 12 may in principle comprise any means of providing fluid communication with the inside of the containers 2 and 3, such as hollow needles, hollow spikes etc. Preferably, if needles or spikes penetrating the septum are used, the needles or spikes are formed so that substantially no residual liquid can be trapped inside the containers 2 and 3.

Housing 10 further comprises coupling means in the form of a third port 13 for releasable coupling of a syringe 20 having a sealing plunger 21 slideably mounted inside. Preferably, the open (distal) end of syringe 20 comprises means for releasably attaching a conduit by a releasable connector, such as a Luer connector of an infusion set. Accordingly, housing 10 comprises corresponding connection means for releasably connecting the syringe 20 to the third port 13.

FIG. 1 further shows a first fluid pathway 14 that enables fluid flow between the first port 11 and the third port 13. Further, the third port 13 and the second port 12 are fluidly connected via a second fluid pathway 15. Also, second port 12 and third port 13 are in fluid communication via a third fluid pathway 16.

At one point along the first fluid pathway 14, a first flow control member 17, preferably in the form of a check valve or non-return valve, is provided resulting in a one-way fluid flow from the first port 11 to the third port 13.

At one point along the second fluid pathway 15, a second flow control member 18, preferably in the form of a check valve or non-return valve, is provided resulting in a one-way fluid flow from the third port 13 to the second port 12 via the second fluid pathway 15.

A third flow control member 19, e.g. in the form of a dial plug, is further provided enabling a user to selectively switch between a first state in which fluid flow is enabled between the first port 11 and the third port 13 via the first fluid pathway 14 and between the third port 13 and the second port 12 via the second fluid pathway 15, and a second state in which fluid flow is enabled between the second port 12 and the third port 13 via the third fluid pathway 16.

At one point along the third fluid pathway 16, a fourth flow control member 22, e.g. in the form of a throttle valve, is provided as a restriction to reduce the flow rate of fluid moving from the second port 12 to the syringe 20. The function of the fourth flow control member 22 will be described in more detail below in the section regarding the operation of the mixing system.

To allow for entry of ambient air into the first container 2 in connection with the transfer of the diluent 8 out of the first container 2 a vent 25 is provided in the transfer unit 5 fluidly connecting the first port 11 with the outside. The first port 11 thus comprises both a fluid pathway dedicated to transfer the diluent 8 out of the first container 2 and a fluid pathway dedicated to allow entry of air into the first container 2.

At one point along the vent 25, a fifth flow control member 23, preferably in the form of a check valve or non-return valve, is provided resulting in a one-way fluid flow from the outside to the first port 11. The vent 25 is further provided with a filter 24 so that no contaminated air is allowed to enter the first container 2.

Figure 2:
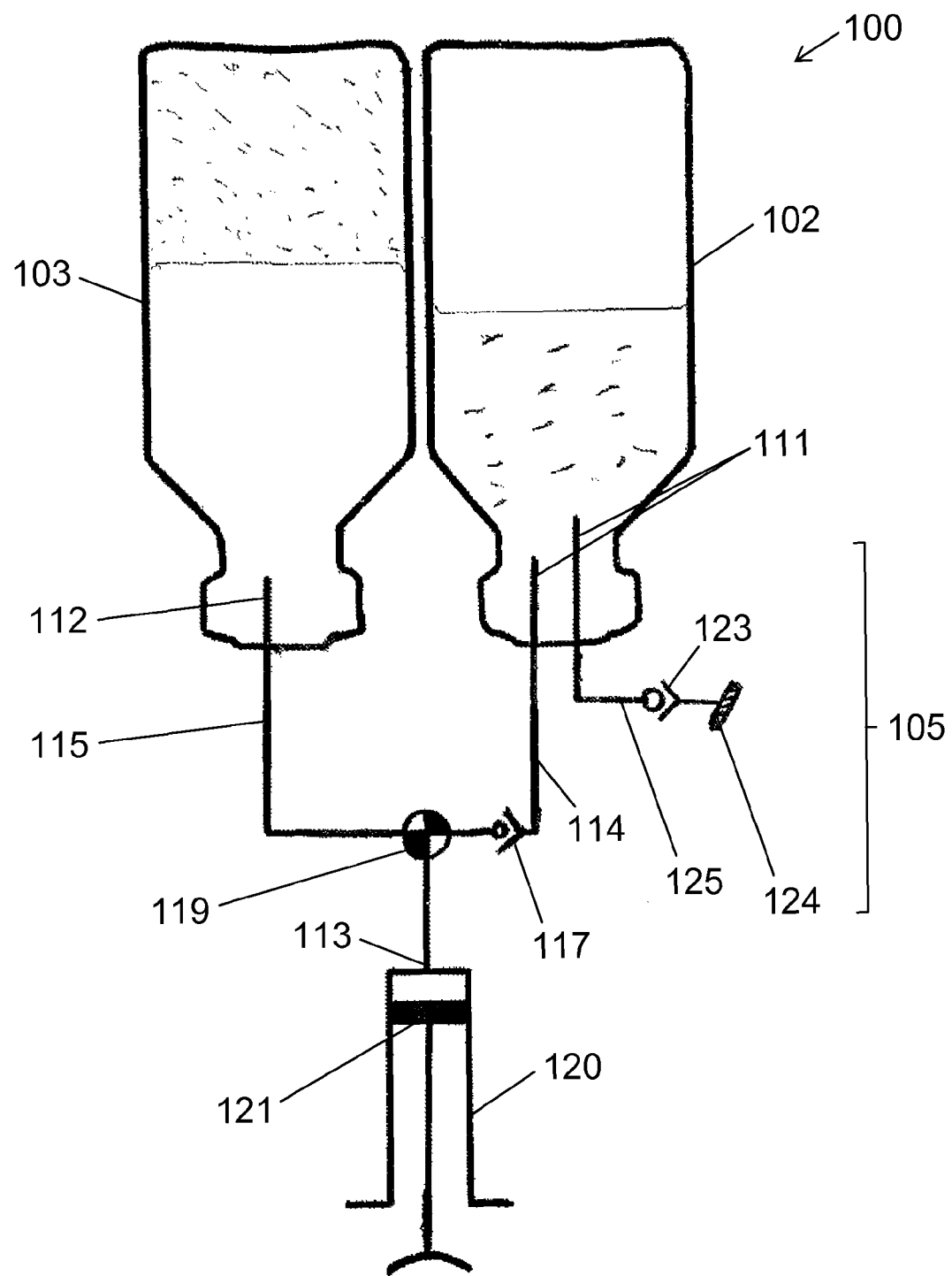
FIG. 2 shows a schematic view of a mixing system according to another embodiment of the invention.

FIG. 2 shows a schematic representation of a mixing system 100 according to an alternative embodiment. In this embodiment a first container 102, containing a predetermined amount of a diluent, a second container 103, containing a predetermined amount of powdered drug, and a syringe 120 having a sealing plunger 121, are connected to a transfer unit 105 in the same manner as described above. A first fluid pathway 114 enables fluid flow between a first port 111 and a third port 113 and a second fluid pathway 115 enables fluid flow between the third port 113 and a second port 112.

A non-return valve 117 is provided in the first fluid pathway 114 resulting in a one-way fluid flow from the first port 111 to the third port 113. Further, a non-return valve 123 is provided in a vent 125 resulting in a one-way fluid flow from the outside through filter 124, to the first container 102.

A third flow control member 119, e.g. in the form of a dial plug, is provided enabling a user to selectively switch between a first state in which fluid flow is enabled between the first port 111 and the third port 113 via the first fluid pathway 114 and a second state in which fluid flow is enabled between the second port 112 and the third port 113 via the second fluid pathway 115.

Figure 3:
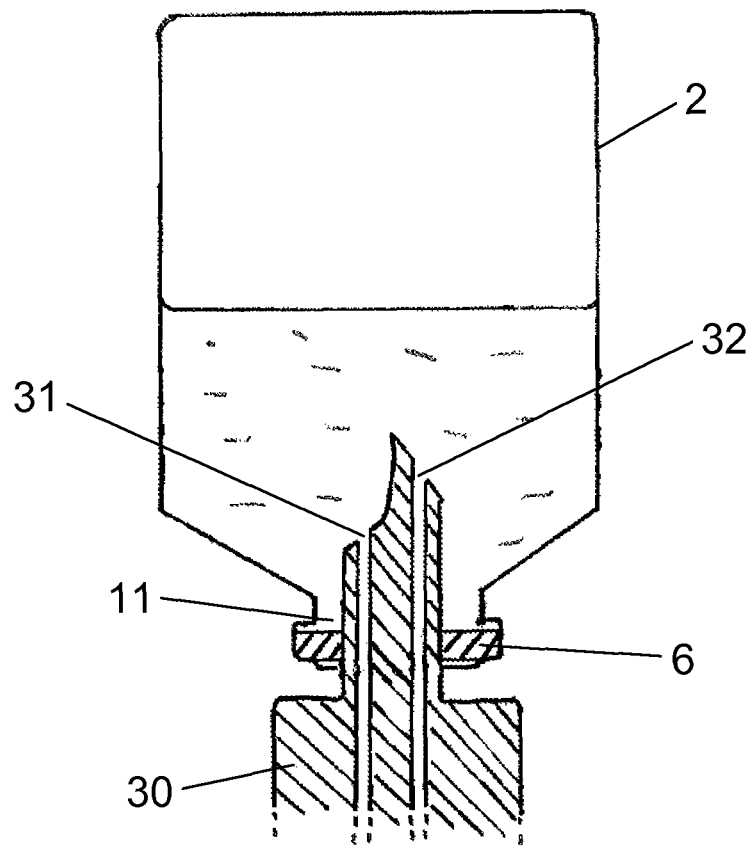
FIG. 3 shows a cross-sectional view of a hollow spike according to an embodiment of the invention.

FIG. 3 shows a first hollow spike 30 serving to establish fluid connection between the first container 2 and the first fluid pathway 14. The first hollow spike 30 comprises two internal channels, a liquid channel 31 dedicated to transfer the diluent 8 out of the first container 2, and an air channel, dedicated to allow vented air to enter the first container 2. The opening of the air channel 32 is axially offset from the opening of the liquid channel 31 to reduce the likelihood of air bubbles entering the liquid channel 31 during transfer of the diluent 8 out of the first container 2. A second hollow spike 57 (see FIG. 7) is used in a like way to establish fluid connection between the second container 2 and the second fluid pathway 15 (also between the second container 2 and the third fluid pathway 16). The second hollow spike 57 is preferably a single channel spike, but it could alternatively be a double channel spike (e.g. one channel for each of the pathways 15, 16 of FIG. 1).

Figure 4:
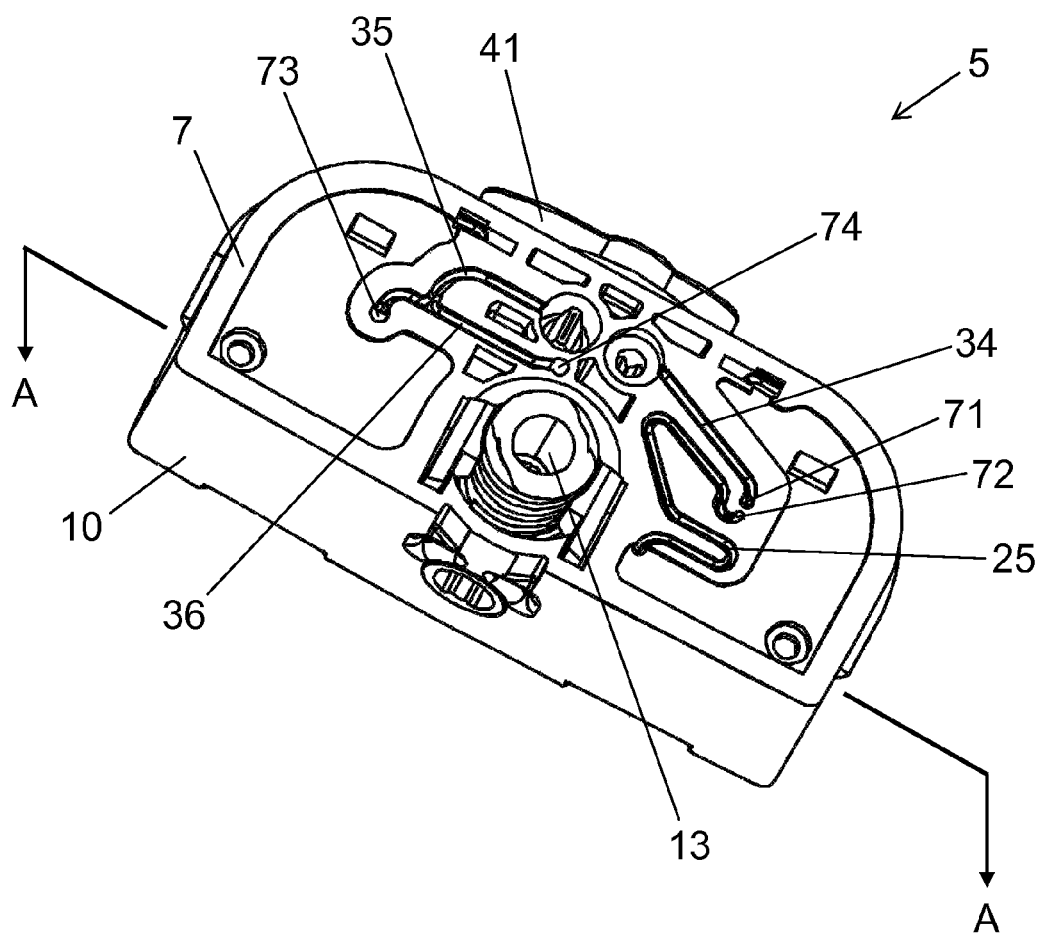
FIG. 4 shows a perspective view of a transfer unit of a mixing system according to an embodiment of the invention.

FIG. 4 shows a perspective view of the transfer unit 5 of FIG. 1, including its various fluid pathways. The first and second hollow spikes 30, 57 are not visible in this view as they protrude from the backside of the transfer unit 5. However, the liquid channel 31 is fluidly connected with a diluent evacuation node 71, and the air channel 32 is fluidly connected with an air inlet node 72. Likewise, the single channel in the second hollow spike 57 is fluidly connected with a mixing node 73. Thereby, fluid flow is enabled between the first port 11 and a first flow channel 34, respectively between the first port 11 and the vent 25, and between the second port 12 and respective second and third flow channels 35, 36. The third flow channel 36 is further fluidly connected with a delivery node 74 through which the administrable drug flows when evacuated from the second container 3 after mixing of the diluent 8 and the powdered drug 9. The flow channels 34, 35, 36 are provided as in-moulded channels in the top face 7 of the housing 10, as shown.

Figure 5A:
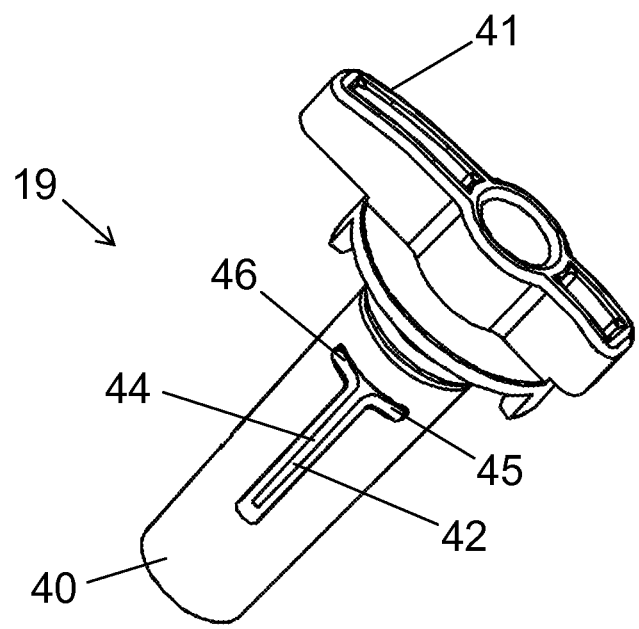
FIGS. 5a and 5b show perspective views of a user operable flow control member according to an embodiment of the invention.
Figure 5B:
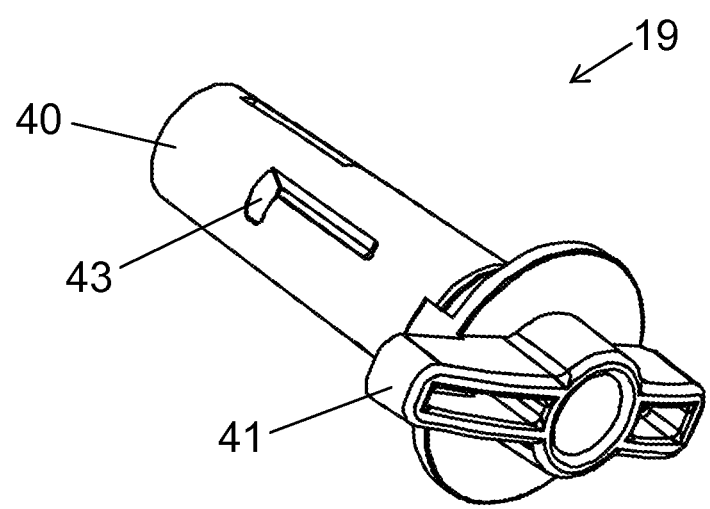

FIGS. 5a and 5b show perspective views of the third flow control member or dial plug 19. Dial plug 19 comprises an elongated plug body 40 and a dial 41 intended for manipulation of the dial plug 19 by a user of the mixing system 1. FIG. 5a shows a first channel segment 42 in the plug body 40 which channel segment 42 constitutes a part of the first fluid pathway 14 fluidly connecting the first port 11 and the third port 13 as well as of the second fluid pathway 15 fluidly connecting the third port 13 and the second port 12, when the dial plug 19 is in a first position. The first channel segment 42 is "T"-shaped and consists of a main portion 44, a first branch 45 and a second branch 46. FIG. 5b shows an "L"-shaped second channel segment 43 in the plug body 40 which channel segment 43 constitutes a part of the third fluid pathway 16 fluidly connecting the second port 12 and the third port 13, when the dial plug 19 is in a second position. Both the first channel segment 42 and the second channel segment 43 are provided as grooves in the dial plug 19.

Figure 6A:
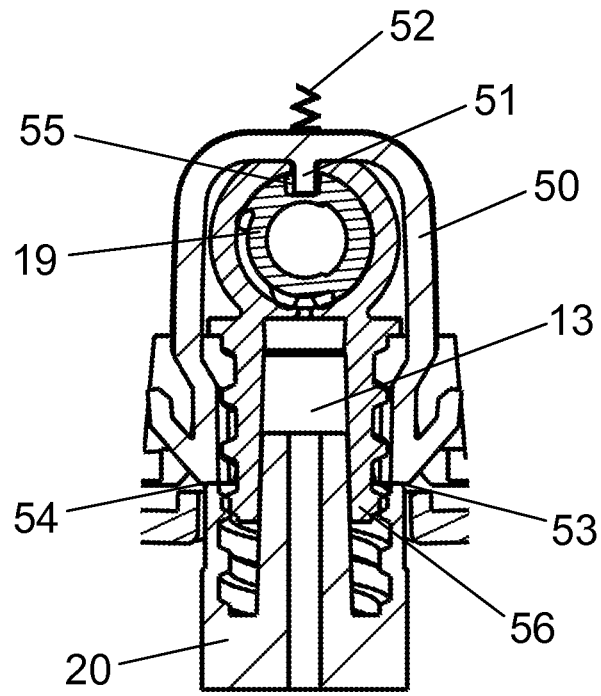
FIG. 6a shows a cross-sectional view of the basic set-up of a locking means according to an embodiment of the invention.

FIG. 6a shows a close-up cross sectional view of the third port 13 highlighting the basic principle of a lock 50 for the third flow control member 19. FIG. 6a shows the syringe 20 (only the distal most portion is shown) just before coupling to a connecting piece 56 at the third port 13. In this position, the syringe 20 touches an abutting surface 54 of the lock 50 in a lock/syringe interface 53. The third flow control member 19 is prevented from rotational movement by a catch member 51 which is biased by a spring means 52 to protrude into a groove 55 in the plug body 40 of the third flow control member 19.

Figure 6B:
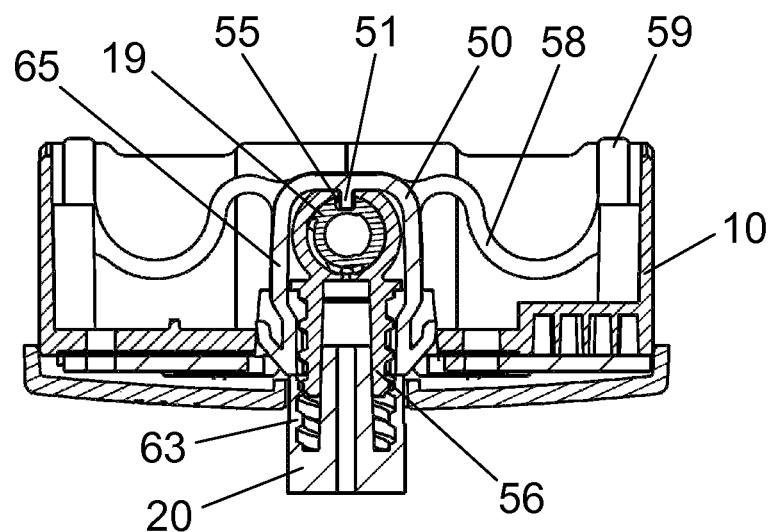
FIGS. 6b-6d show cross-sectional views of the operating principle of a locking means according to an embodiment of the invention.

FIG. 6b shows a cross sectional view A-A (see FIG. 4) corresponding to the view of FIG. 6a. The lock 50 has a flexible structure and comprises a couple of "S"-shaped arms 58 extending laterally from a central piece 65. The arms 58 terminate in peripheral parts of the housing 10 and are supported (not shown) at their respective ends 59 in such a manner that the ends 59 are prevented from moving relative to the housing 10. A collar 63 of the syringe 20 only just abuts the central piece 65.

Figure 6C:
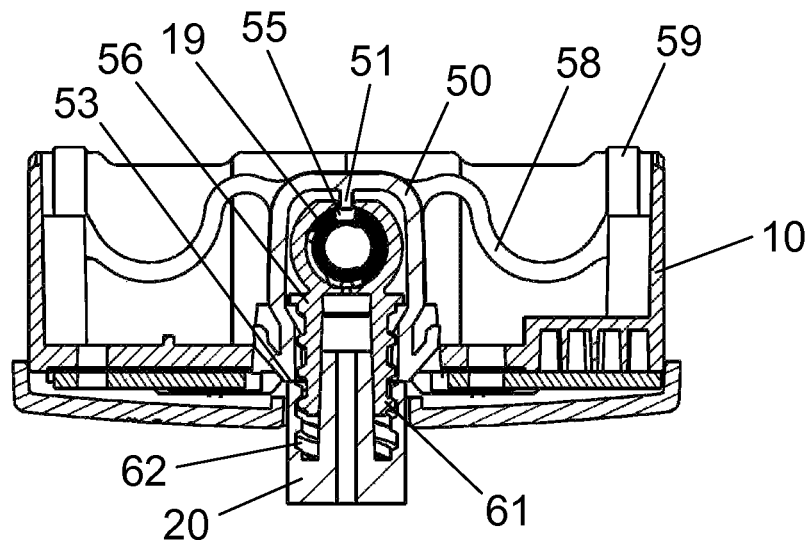
Figure 6D:
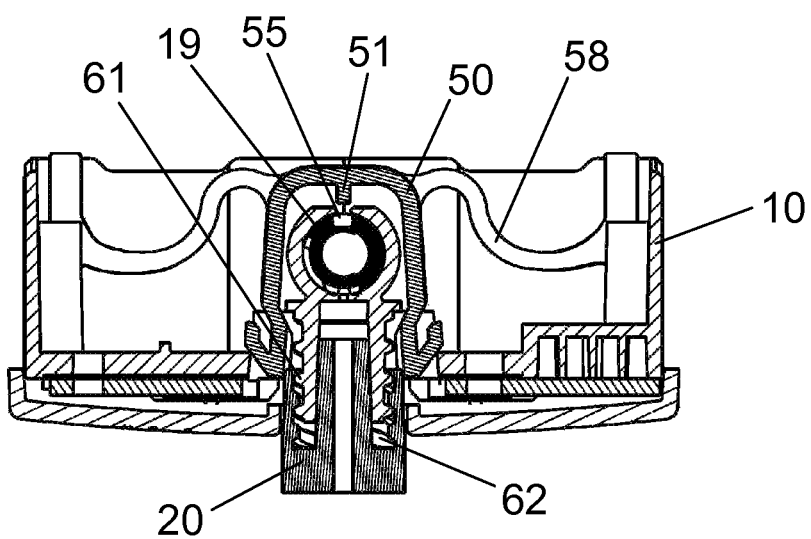

FIGS. 6c and 6d show different stages of engagement between an inner thread 62 in the collar 63 and an outer thread 61 on the connecting piece 56. As the lock/syringe interface 53 is moved gradually inwards away from the opening of the third port 13 as a consequence of the syringe 20 being screwed onto the connecting piece 56, the biasing force of the arms 58 is overcome and the arms 58 are deflected, whereby the catch member 51 is carried completely out of engagement with the groove 55 (FIG. 6d). When the syringe 20 is tightly fastened to the third port 13, the third flow control member 19 is free to be rotated and thereby to switch between the first state in which fluid flow is enabled between the first port 11 and the third port 13 via the first fluid pathway 14 and between the third port 13 and the second port 12 via the second fluid pathway 15, and the second state in which fluid flow is enabled between the second port 12 and the third port 13 via the third fluid pathway 16.

Similarly, with reference to FIG. 2, when the syringe 20 is tightly fastened to the third port 13, the third flow control member 19 is free to be rotated and thereby to switch between enabling fluid flow between the first port 11 and the third port 13 and between the second port 12 and the third port 13.

Because of the resilient structure of the lock 50 and the retained ends 59 if the syringe 20 is detached from the third port 13 while the third flow control member 19 is in a position corresponding to the first state the arms 58 will return to their initial positions and thereby force the catch member 51 back into engagement with the groove 55. This ensures that the third flow control member 19 can not be rotated to switch from the first state to the second state unless a syringe is coupled to the third port 13.

A Luer lock connection between the syringe 20 and the connecting piece 56 at the third port 13 is just one example of a fitting between the syringe 20 and the third port 13. Other non-limiting examples include, e.g., a snap fit coupling or a bayonet coupling.

Figure 7:
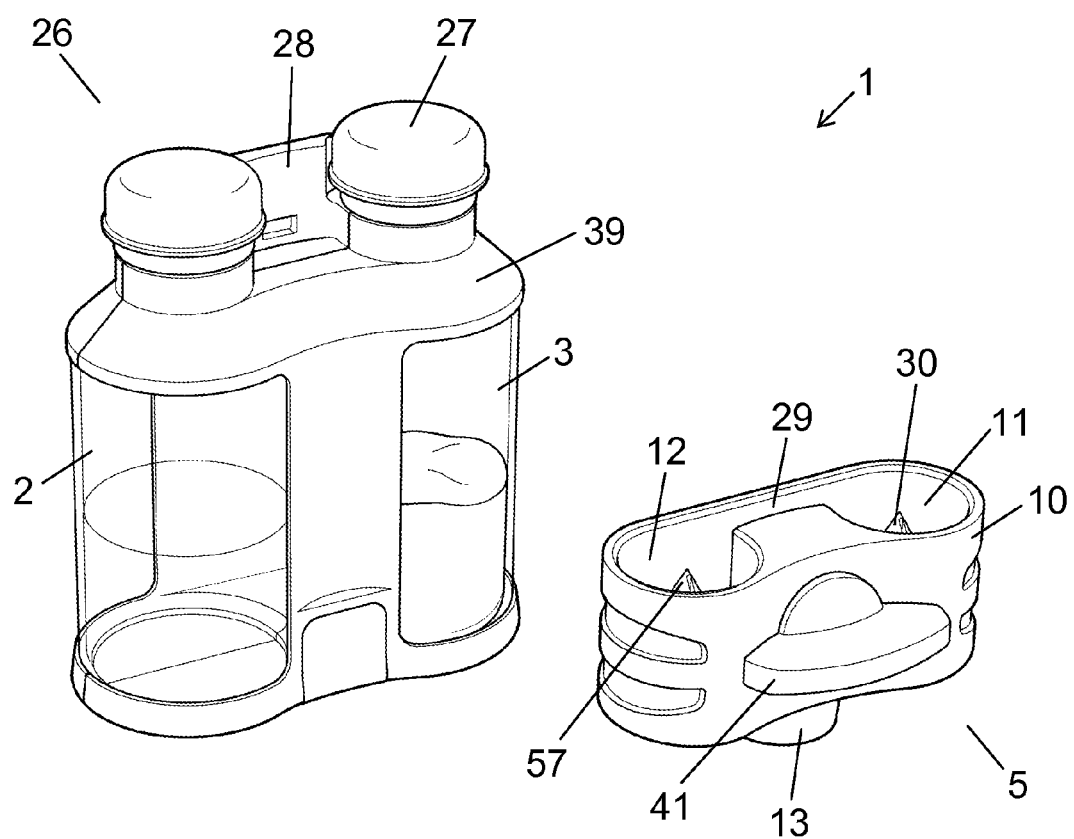
FIG. 7 shows a perspective view of a mixing system according to an embodiment of the invention in a disassembled state.

FIG. 7 is a perspective view of a disassembled mixing system 1 according to an embodiment of the invention. The mixing system 1 comprises a container unit 26 and a transfer unit 5 as described in detail above, the container unit 26 and the transfer unit 5 being adapted to be coupled together to form the drug mixing system 1.

The container unit 26 comprises a housing 39, a first container 2 containing first contents in the form of a diluent, and a second container 3 containing second contents in the form of a dry drug. The containers 2, 3 are fixed in the housing 39, and it is thereby ensured that the first contents and the second contents match, e.g. in terms of amount and kind. Each of the containers 2, 3 is provided with a removable cap 27.

The container unit 26 is provided with a wall part 28 which is arranged asymmetrically on the housing 39. The transfer unit 5 is provided with a corresponding groove 29 adapted to accommodate the wall part 28. Thereby it is ensured that it is only possible to couple the container unit 26 and the transfer unit 5 in such a manner that the first port 11 is coupled to the first container 2 and the second port 12 to the second container 3, and not vice versa. Accordingly, it is ensured that the fluid flows in the assembled mixing system 1 are correct.

The transfer unit 5 comprises a first port 11 adapted to receive the first container 2, a second port 12 adapted to receive the second container 3, and a third port 13 adapted to receive a syringe (not shown). The transfer unit 5 is further provided with a number of flow channels (not visible) connecting the ports 11, 12, 13 in such a manner that, when the transfer unit 5 and the container unit 26 are coupled together, the diluent is allowed to move from the first container 2 to a syringe coupled to the third port 13, from the syringe on to the second container 3 in order to allow the diluent and the dry drug to mix, and in such a manner that the mixed material is subsequently allowed to move to the syringe. The spikes 30, 57 of the ports 11, 12 are also shown.

Figure 8:
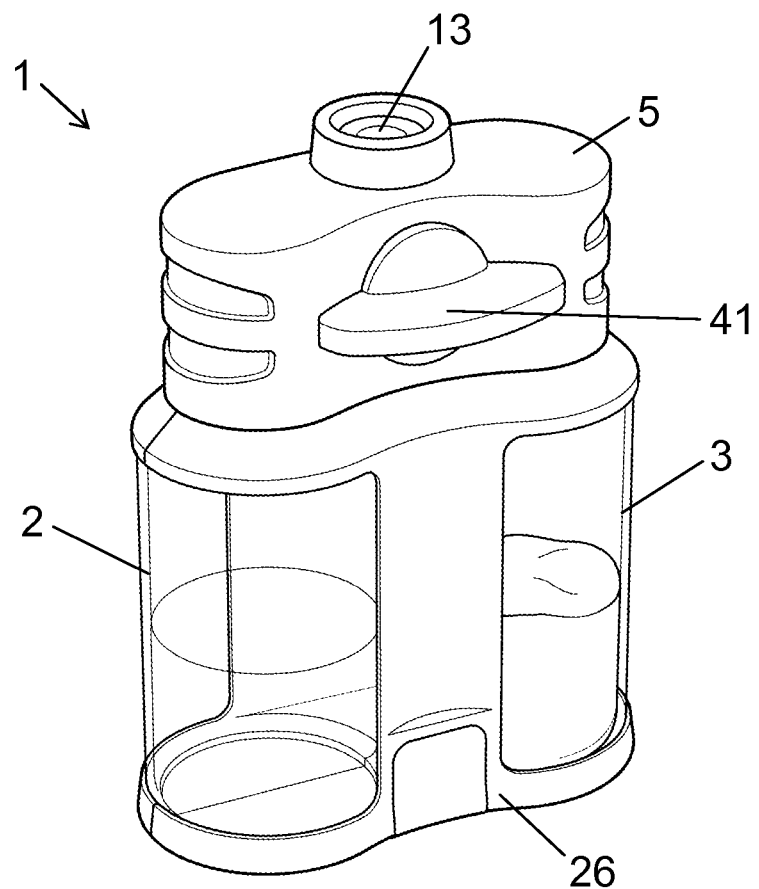
FIG. 8 shows a perspective view of the mixing system of FIG. 7 in an assembled state.

FIG. 8 is a perspective view of the mixing system 1 of FIG. 7 in an assembled state.

Operation of the Mixing System

The mixing system of FIG. 1 comprising the various structures and features of the components shown in FIGS. 3-8 may be operated in the following manner. When it is desired to mix the diluent 8 and the powdered drug 9, the caps 27 are removed and the transfer unit 5 is connected to the container unit 26 in such a manner that the first container 2 is received in the first port 11 and the second container 3 is received in the second port 12.

In practice, the first hollow spike 30 will thereby penetrate the membrane 6 of the first container 2 to establish fluid connection between the first container 2 and the first fluid pathway 14. Similarly, the second hollow spike 57 will penetrate the membrane (not shown) of the second container 3 to establish fluid connection between the second container 3 and the second fluid pathway 15.

The syringe 20 with a fully, or substantially fully, advanced plunger 21 is then coupled to the third port 13. The transfer unit is provided by the manufacturer in a ready-to-use condition, i.e. where the dial plug 19 is in a position corresponding to the first state in which fluid flow is enabled between the first port 11 and the third port 13 via the first fluid pathway 14 and between the third port 13 and the second port 12 via the second fluid pathway 15.

The mixing system 1 is held vertically so that the two containers 2 and 3 are positioned above the syringe 20, and the plunger 21 is pulled back. This will cause the check valve 17 to open while the check valve 18 remains closed. Accordingly, the diluent 8 is sucked out of the first container 2 and transferred to the syringe 20 via the liquid channel 31, the diluent evacuation node 71, the first flow channel 34, the first branch 45, and the main portion 44. The check valve 18 ensures that air or material is not sucked from the second container 3 into the syringe 20 during this operation. Further, ambient air is sucked into the first container 2 via the vent 25, the air inlet node 72, and the air channel 32. When the mixing system is held in this position, the opening of the air channel 32 in the first hollow spike 30 is arranged above the opening of the liquid channel 31. This ensures that no, or a minimum of, air bubbles are transferred along with the diluent 8 from the first container 2 to the syringe 20.

When a sufficient amount of the diluent 8, e.g. all of the diluent 8, has been transferred to the syringe, the plunger 21 is pushed forward. This will close the check valve 17 and open the check valve 18 to allow transfer of the diluent 8 from the syringe 20 to the second container 3 via the main portion 44, the second branch 46, the second flow channel 35, the mixing node 73, and the second hollow spike 57. The transfer of the diluent 8 into the second container 3 causes an increase in pressure in the second container 3. The check valve 18 and the dial plug 19, being in a position corresponding to the first state, prevent any of the diluent 8 and the powdered drug 9 from leaving the second container 3.

When the diluent 8 and the powdered drug 9 have mixed properly to form a drug solution, the dial 41 is turned, e.g. approximately 90 degrees. This will result in the dial plug 19 switching from the first state to the second state in which fluid flow is enabled between the second port 12 and the third port 13 via the third fluid pathway 16. The increased pressure in the second container 3 will drive some or all of the drug solution out of the second container 3 and into the syringe 20 via the second hollow spike 57, the mixing node 73, the third flow channel 36, the delivery node 74, and the second channel segment 43. If not all of the drug solution is forced out of the second container 3 and into the syringe 20 by means of the increased pressure in the second container 3, the plunger 21 may be manually retracted in addition to ensure that the second container 3 is being emptied. Importantly, when the dial plug 19 is in the second state fluid flow is disabled between the first port 11 and the third port 13. This ensures that no unwanted residual contents of the first container 2 or potentially contaminating ambient air can accidentally be sucked into the syringe 20 to mix with the drug solution when the user prepares for delivery by transferring the administrable drug from the second container 3 to the syringe 20.

The above described transfer of drug solution from the second container 3 to the syringe 20 due to the increased pressure in the second container 3 may be executed so fast that the drug solution begins to foam. The throttle valve 22 in the third fluid pathway 16 eliminates this risk by reducing the flow rate of the drug solution to a level where foaming will not take place. Avoiding foaming is highly important for several kinds of drugs, in particular drugs that must be administered intravenously.

The fact that the system can be left in the first state for a period of time is of high importance to the user if he needs to mix further doses from similar mixing systems (so-called "pooling" as mentioned earlier) before infusing the drug. In case, a person needs to reconstitute more drug than what is provided in a single powdered drug container, a number of mixing systems can be prepared to the step where the diluent has been transferred to the second container and mixed with the powdered drug. The individual containers containing the final drug solutions can then be emptied successively by successively coupling a syringe to each of the third ports and turning the respective dials to allow the mixed contents to be forced out of the pressurised containers. All the prepared doses can then e.g. be accumulated in the same syringe and infused or injected in one go, which is highly preferable for the users, in particular patients requiring intravenous infusion.

As can be understood from the above operational steps, the invention provides a mixing system which is extremely simple and efficient for users to operate.

Figure 9:
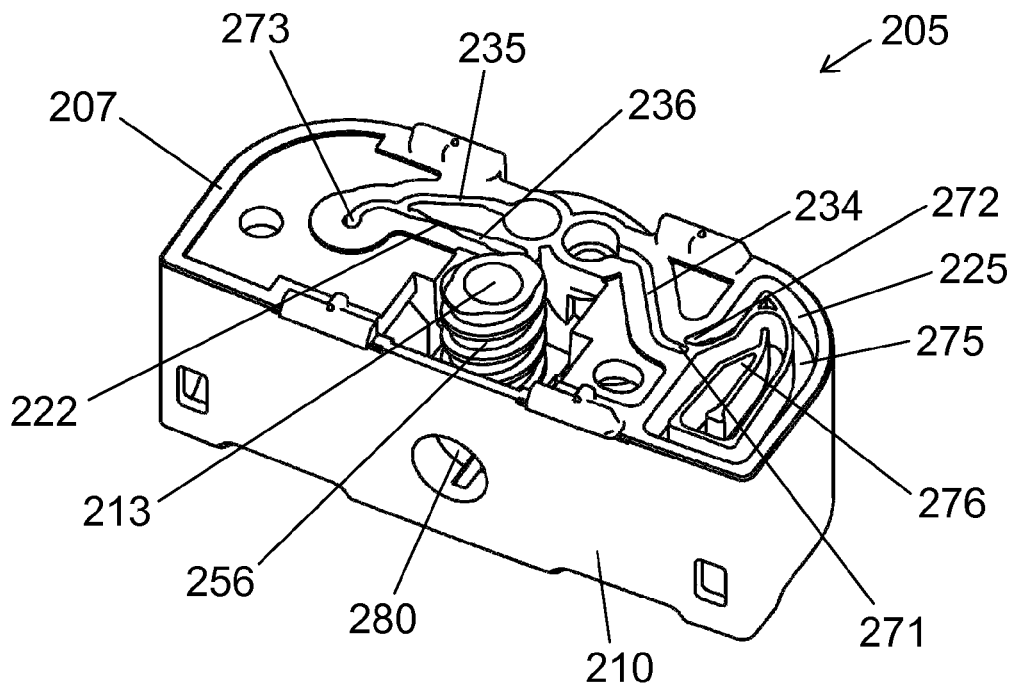
FIG. 9 shows a perspective view of a transfer unit according to another embodiment of the invention.

FIG. 9 shows, in an alternative embodiment, a transfer unit 205 for use in the mixing system 1. The basic functionality of the transfer unit 205 is similar to the functionality of the previously described transfer unit 5. However, this embodiment of the transfer unit 205 offers an additional feature which will be apparent from the following description.

The transfer unit 205 has a housing 210 with a top face 207 comprising a number of in-moulded channels. A first hollow spike (not visible) protruding from the backside of the transfer unit 205 is adapted to establish fluid connection with a diluent container (not shown) when the diluent container is received in a first port (not visible). This spike has a liquid channel (not visible) and an air channel (not visible) similar to the first hollow spike 30 described above. The liquid channel is fluidly connected with a diluent evacuation node 271 which is further fluidly connected with a first flow channel 234. The air channel is fluidly connected with a vent 225 which is arranged to also provide a reservoir 275 capable of containing a volume of liquid. The reservoir 275 is formed as a serpentine channel extending from an air inlet node 272 to a serpentine end 276. A second hollow spike (not visible) protruding from the backside of the transfer unit 205 is adapted to establish fluid connection with a powder container (not shown) when the powder container is received in a second port (not visible). This spike has a single channel (not visible) which is fluidly connected with a mixing node 273 which is in turn fluidly connected with, respectively, a second flow channel 235 and a third flow channel 236. The third flow channel 236 comprises a constriction 222 for controlling the flow rate of the mixed product during transport from the second container to a syringe (not shown), when the syringe is attached to the transfer unit 205. A connecting piece 256 at a third port 213 provides an interface for coupling with such a syringe. FIG. 9 also discloses a bore 280 adapted to house the user operable flow control member (not shown).

Figure 10:
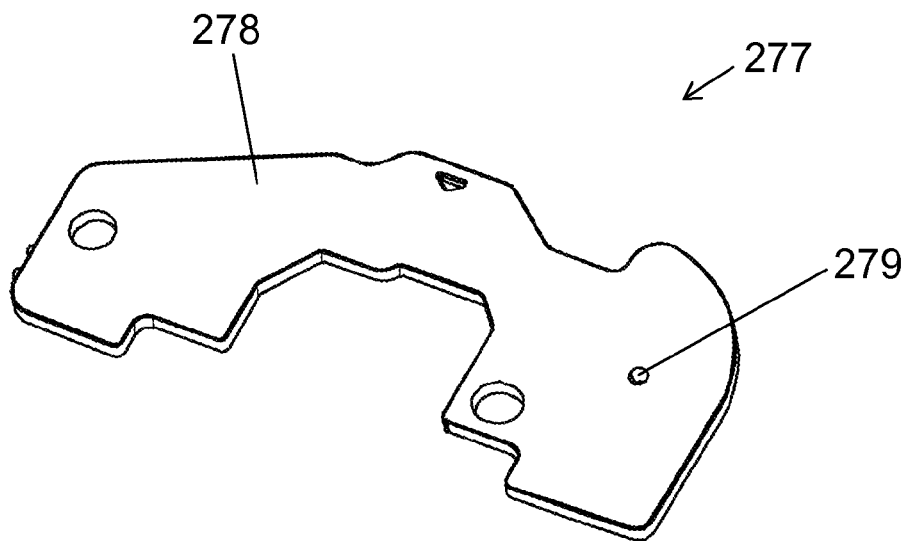
FIG. 10 shows a perspective view of a cover plate for the transfer unit of FIG. 9, FIGS. 11a and 11b show perspective views of a user operable flow control member according to another embodiment of the invention.

FIG. 10 shows a perspective view of a sealing cover 277 adapted for permanent attachment, e.g. by gluing or welding, to the top face 207 to seal the various channels in the transfer unit 205. The sealing cover comprises a plate 278 having a configuration which enables a complete coverage of the channels in question. A small hole 279 is arranged in the plate 278 in such a manner that when the plate 278 is attached to the top face 207 the hole 279 is positioned just above the serpentine end 276.

In use, when the transfer unit 205 is coupled to the container unit 26 an excess pressure may build up inside the first container 2 during penetration of the membrane 6 by the first hollow spike. If this happens a small volume of diluent 8 will be forced through the air channel and into the vent 225. However, as the vent 225 is formed to comprise the reservoir 275 the diluent 8 will merely accumulate in the reservoir 275.

When a negative pressure is generated in the first container 2, as a consequence of the plunger 21 in the syringe 20 which is coupled to the third port 213 being retracted, air will be sucked into the vent 225 through the hole 279 above the serpentine end 276 and will enter the first container 2 along with the accumulated volume of diluent 8. From here this volume of diluent 8 will simply be evacuated along with the rest of the diluent 8 into the first flow channel 234 and further on to the syringe 20. The arrangement of the reservoir 275 as a serpentine channel, whereby a tortuous path is provided from the air inlet node 272 to the serpentine end 276, and the position of the hole 279 above the serpentine end 276 minimise the risk that the escaped diluent 8 will leak out of the transfer unit 205 through the hole 279.

Figure 11A:
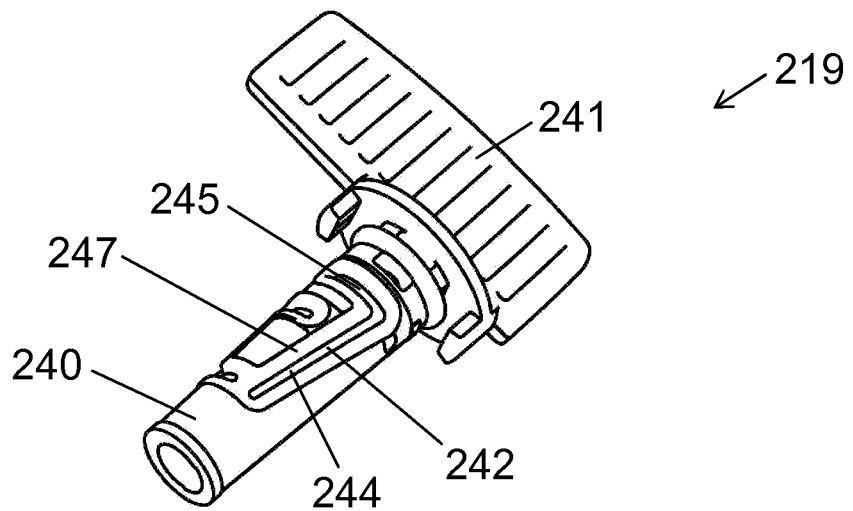
Figure 11B:
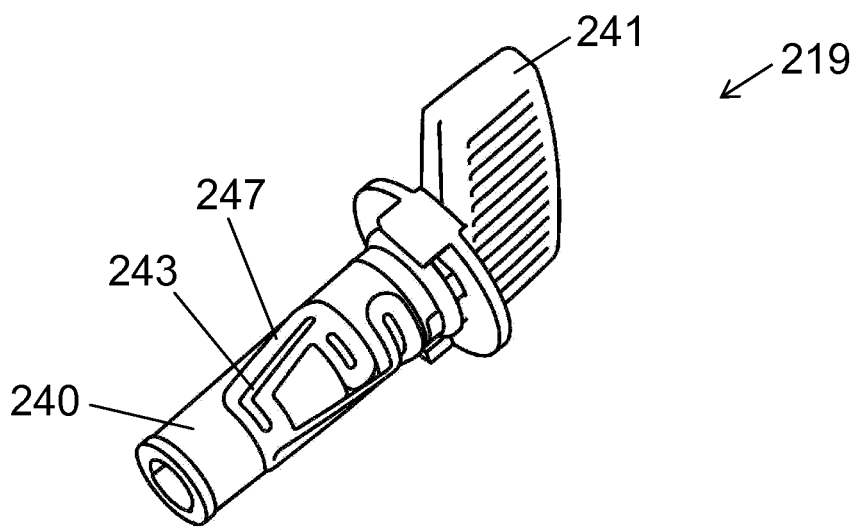

FIGS. 11a and 11b show perspective views of an alternative embodiment of a third flow control member, for use in a transfer unit of the mixing system 1, having the same function as the above described. Dial plug 219 comprises a conical plug body 240 and a dial 241 intended for manipulation of the dial plug 219 by a user of the mixing system 1. FIG. 11a shows a first channel segment 242 in the plug body 240 which channel segment 242 constitutes a part of the first fluid pathway 14 fluidly connecting the first port 11 and the third port 13 as well as of the second fluid pathway 15 fluidly connecting the third port 13 and the second port 12, when the dial plug 219 is in a first position. The first channel segment 242 consists of a main portion 244 and a first branch 245. During transport of material from the first port 11 to the third port 13 the material flows through the first branch 245 and the main portion 244, whereas during transport of the material from the third port 13 to the second port 12 the material only flows through the main portion 244 (in the opposite direction of the flow to the third port 13). FIG. 11b shows a second channel segment 243 in the plug body 240 which channel segment 243 constitutes a part of the third fluid pathway 16 fluidly connecting the second port 12 and the third port 13, when the dial plug 219 is in a second position. The channel segments 242, 243 are provided between lips 247 of material which has been bound to the plug body 240, e.g. by two-component moulding, and which provides for a fluid tight fit of the plug body 240 in the transfer unit housing. The lips 247 are of a softer, more flexible material than the plug body 240 which further results in a low friction interface between the plug body 240 and the transfer unit housing, making the third flow control member 219 easy to operate even for a user with limited dexterity.

Figure 12:
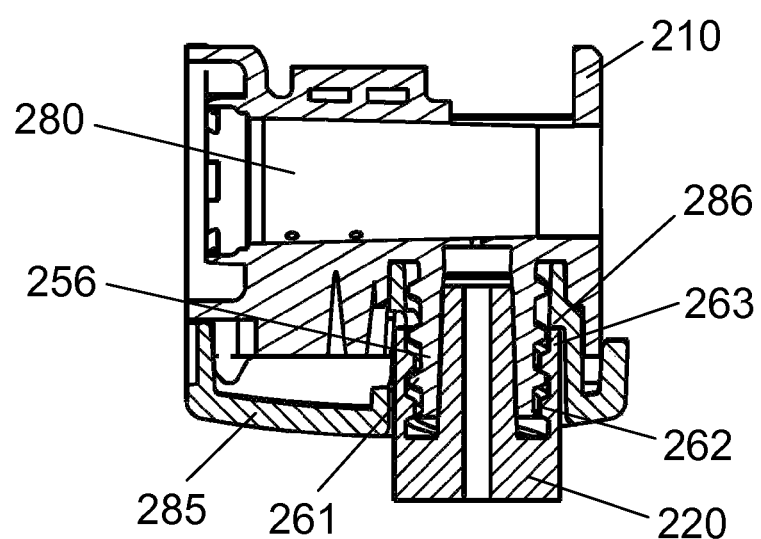
FIG. 12 shows a cross-sectional view of a stop defining arrangement according to an embodiment of the invention.

FIG. 12 shows a cross sectional side view of the transfer unit 205 and illustrates a stop arrangement according to an aspect of the invention. In the figure a syringe 220 (only the distal most portion is shown) has been attached to the connecting piece 256 by mating an inner screw thread 262 of a syringe collar 263 with an outer screw thread 261 of the connecting piece 256. The syringe 220 has thereby been screwed onto the connecting piece 256 to a point where the collar 263 abuts a contact face 286 of an outer cover 285 adapted to protect the top face 207 of the transfer unit 205. The contact face 286 thus provides a stop for further mounting movement of the syringe 220 relative to the housing 210. Hereby, it is ensured that the user does not risk accidentally breaking the conical open end portion of the syringe 220 by excessively forcing the syringe 220 onto the connecting piece 256, e.g. due to an uncertainty of whether proper attachment has been attained.

In the above description of the exemplary embodiments, the different structures providing the desired relations between the different components just as the means providing the described functionality for the different components of a transfer system have been described to a degree to which the concept of the present invention will be apparent to the skilled reader. The detailed construction and specification for the different structures are considered the object of a normal design procedure performed by the skilled person along the lines set out in the present specification.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A transfer unit for a medical mixing system comprising:
   a first port adapted to receive a first container containing first contents,
   a second port adapted to receive a second container containing second contents,
   a third port adapted to receive a syringe,
   a first fluid pathway that enables fluid flow between the first port and the third port,
   a second fluid pathway that enables fluid flow between the third port and the second port,
   a third fluid pathway that enables fluid flow between the second port and the third port,
   a first flow control member disposed between the first port and the third port, enabling one-way fluid flow from the first port to the third port when a syringe is coupled to the third port,
   a second flow control member disposed between the third port and the second port, enabling one-way fluid flow from the third port to the second port when a syringe is coupled to the third port, and
   a third flow control member,
   wherein the third flow control member provides for user selective switching between a first state in which fluid flow is enabled between the first port and the third port via the first fluid pathway and between the third port and the second port via the second fluid pathway, and a second state in which fluid flow is enabled between the second port and the third port via the third fluid pathway but disabled between the first port and the third port; and
      the transfer unit for a medical mixing system further comprises a lock for ensuring that the third flow control member can only be manipulated when a syringe is coupled to the third port.

2. A transfer unit for a medical mixing system according to claim 1, wherein the lock is adapted to engage with the third flow control member to prevent movement of the third flow control member, and wherein the lock is configured to disengage with the third flow control member in response to a syringe being coupled to the third port.

3. A transfer unit for a medical mixing system according to claim 2, wherein the lock is further configured to re-engage with the third flow control member in response to the syringe being decoupled from the third port.

4. A transfer unit for a medical mixing system according to claim 3, wherein the lock comprises a biasing structure and a catch member adapted to move into and out of engagement with a related catch member in the third flow control member.

5. A transfer unit for a medical mixing system according to claim 1, wherein the third flow control member comprises a first channel segment constituting a part of the first fluid pathway and a part of the second fluid pathway, and a second channel segment constituting a part of the third fluid pathway.

6. A transfer unit for a medical mixing system according to claim 5, wherein the first channel segment and the second channel segment are defined by at least one ridge.

7. A transfer unit for a medical mixing system according to claim 1, further comprising a reservoir in fluid communication with the first port.

8. A transfer unit for a medical mixing system according to claim 7, wherein the reservoir comprises a serpentine channel in fluid communication with ambient air.

9. A transfer unit for a medical mixing system according to claim 1, further comprising a fourth flow control member adapted to restrict a flow rate in the third fluid pathway.

10. A transfer unit for a medical mixing system according to claim 1, wherein the first port comprises an asymmetric hollow spike or needle having two internal channels, and openings of the asymmetrical hollow spike or needle are axially offset.

11. A medical mixing system comprising:
a first container containing first contents,
a second container containing second contents, and
a transfer unit for a medical mixing system comprising: a first port adapted to receive the first container containing first contents, a second port adapted to receive the second container containing second contents, a third port adapted to receive a syringe, a first fluid pathway that enables fluid flow between the first port and the third port, a second fluid pathway that enables fluid flow between the third port and the second port, a third fluid pathway that enables fluid flow between the second port and the third port, a first flow control member disposed between the first port and the third port, enabling one-way fluid flow from the first port to the third port when a syringe is coupled to the third port, a second flow control member disposed between the third port and the second port, enabling one-way fluid flow from the third port to the second port when a syringe is coupled to the third port, and a third flow control member, wherein the third flow control member provides for user selective switching between a first state in which fluid flow is enabled between the first port and the third port via the first fluid pathway and between the third port and the second port via the second fluid pathway, and a second state in which fluid flow is enabled between the second port and the third port via the third fluid pathway but disabled between the first port and the third port; and the transfer unit for a medical mixing system further comprises a lock for ensuring that the third flow control member can only be manipulated when a syringe is coupled to the third port.

12. A medical mixing system according to claim 11, wherein the first container and the second container are arranged in a container unit holding the first container and the second container in a mutually fixed position.

13. A medical mixing system according to claim 12, wherein the container unit and the transfer unit for a medical mixing system are shaped in such a manner that the container unit and the transfer unit for a medical mixing system can only be coupled together when positioned in a predetermined mutual orientation.

* * * * *